United States Patent [19]

Schulze, Sr. et al.

[11] 4,196,628
[45] Apr. 8, 1980

[54] PORTABLE PSYCHROMETRIC TEST APPARATUS AND METHOD FOR AIR CONDITIONING EQUIPMENT

[75] Inventors: James L. Schulze, Sr., Louisville; Wallace Shakun, Prospect, both of Ky.

[73] Assignee: General Electric Company, Louisville, Ky.

[21] Appl. No.: 2,427

[22] Filed: Jan. 10, 1979

[51] Int. Cl.² .......................................... G01K 13/02
[52] U.S. Cl. .................................. 73/432 R; 62/129; 73/336; 73/338.6
[58] Field of Search ................. 73/112, 335, 336, 338, 73/338.6, 349, 190 R, 432 R; 62/129, 130

[56] References Cited

U.S. PATENT DOCUMENTS 3,605,495  9/1971  Krause .................................. 73/198

FOREIGN PATENT DOCUMENTS 709911  6/1954  United Kingdom ...................... 73/335
734702  8/1955  United Kingdom ...................... 73/349

Primary Examiner—S. Clement Swisher
Assistant Examiner—Denis E. Corr
Attorney, Agent, or Firm—Frank P. Giacalone; Radford M. Reams

[57] ABSTRACT

A portable in situ psychrometric test apparatus and method for determining, without the use of standard environmental test rooms, the capacity that an air conditioner would exhibit when operated under predetermined standard environmental test conditions. Mutually isolated air flow chambers are detachably mounted to the air intake and air discharge openings of the conditioner. Samples of air flowing through the chambers under normal operation of the conditioner are withdrawn and wet bulb/dry bulb measurements taken at the end of a predetermined operating period. Air velocity through the chambers and condenser environmental air dry bulb temperature are also measured. These measurements give in situ operating capacity which is then converted, using predetermined empirically derived correction factors, to operating capacity under standard environmental conditions.

9 Claims, 6 Drawing Figures

PORTABLE PSYCHROMETRIC TEST APPARATUS AND METHOD FOR AIR CONDITIONING EQUIPMENT

This invention relates to simplified apparatus and method useful in performing in situ tests to determine the operating capacity and energy efficiency that an air conditioner would exhibit under standard environmental test conditions in a substantially reduced amount of time as compared with conventional test procedures and without the necessity for employing costly standard environmental test rooms in conducting such tests.

The operating performance of an air conditioner (heating and/or cooling) is conventionally specified in terms of its operating capacity for the addition or removal of heat from the conditioned air and is usually expressed in BTU's per hour or its equivalent in tons per hour. It is the practice in the industry to express rated capacity in terms of that capacity which would be exhibited when operating under industry standard environmental test conditions.

For example, it is conventional in the case of cooling air conditioners to utilize standard conditions established by the Association of Home Appliance Manufacturers (AHAM). In the case of a cooling conditioner, these standards specify temperatures on the evaporator or indoor air side of the conditioner of 67° F. as measured with a wet bulb thermometer and 80° F. as measured with a dry bulb thermometer. On the outdoor or condenser side, the temperature specifications are 73° F. wet bulb and 95° F. dry bulb.

With the onset of concern over energy usage, it is also now important to know and specify the energy efficiency ratio (EER) of air conditioners. The EER is conventionally determined by dividing the test operating capacity by the watts of energy input.

United States Government is currently considering the establishment of regulations that would require the manufacturer to specify capacity and EER on rating labels attached to the air conditioner to assist the consumer in making an informed purchase, and it is likely that other countries will follow suit. It is conventional practice in commercial manufacturing operations to test random samples of production units, e.g. two or three per day, to assure compliance with specificed ratings for capacity and EER. Additionally, certain clarifications of the proposed regulations are under consideration that are likely to require a much higher test sample population than currently used in order to provide satisfactory evidence of compliance with the proposed rating label regulations. The purpose, of course, is to assure that the mass produced units, even though designed to meet certain rating specifications, do in fact perform as rated, within acceptable limits of statistical variation from the nominal rating.

A problem with conventional test procedures, and a major reason for heretofore relying on such a small test sample population, lies in the cost and complexity of the test equipment required to establish operation under the standard environmental test conditions. For exaple, relatively large test chambers as well as bulky and costly equipment are required to maintain the environmental temperature and humidity at the standard AHAM conditions and to obtain the necessary physical measurements relating to performance. Additionally, a substantial amount of operating time, such as two hours, has been considered necessary to bring the unit under test up to a stable condition of operation which would give reliable test results. It is obvious that such cumbersome and time consuming test procedures do not lend themselves well to large volume testing on a mass production line nor is it possible to conveniently test units in the field with such procedures.

It is, therefore, an object of this invention to provide a simple, inexpensive, portable apparatus and method to test for operating capacity and efficiency that can be employed on air conditioners without the need to remove and place the units in standard environmental test chambers.

Another object is to provide a portable device and method enabling 100% testing of air conditioners on a production line for compliance with energy rating label regulations.

SUMMARY OF INVENTION

In accordance with the present invention, there is provided a portable in situ psychrometric test apparatus and method for determining, without the use of standard environmental test rooms, the capacity that an air conditioner would exhibit when operated under predetermined standard environmental test conditions. The test apparatus comprises, in part, air flow means for passing intake and discharge evaporator air therethrough in response to normal operation of the air conditioner with the air flow means having two air flow chambers, mutually isolated and adapted to be detachably secured in air sealed manner to the evaporator air side of the air conditioner by suitable latch means provided for that purpose. Samples of air flowing through these chambers are withdrawn and passed over means for measuring the wet bulb and dry bulb temperature of each sample at the end of a predetermined period of operation of the air conditioner. Means for measuring velocity of air flow is provided in at least one of the air flow chambers and means are further provided for measuring the dry bulb temperature of the environmental air outside the air flow chambers at the condenser air intake, wherein these measurements are also made at end of the aformentioned predetermined time period. From these measurements, the in situ operating capacity of the air conditioner can be determined using well known thermodynamic relationships and then converted to operating capacity under standard operating conditions by application of a predetermined correction factor derived empirically from multiple tests of a similar design air conditioner taken under the standard environmental test conditions.

DETAILED DESCRIPTION

Figure 1:
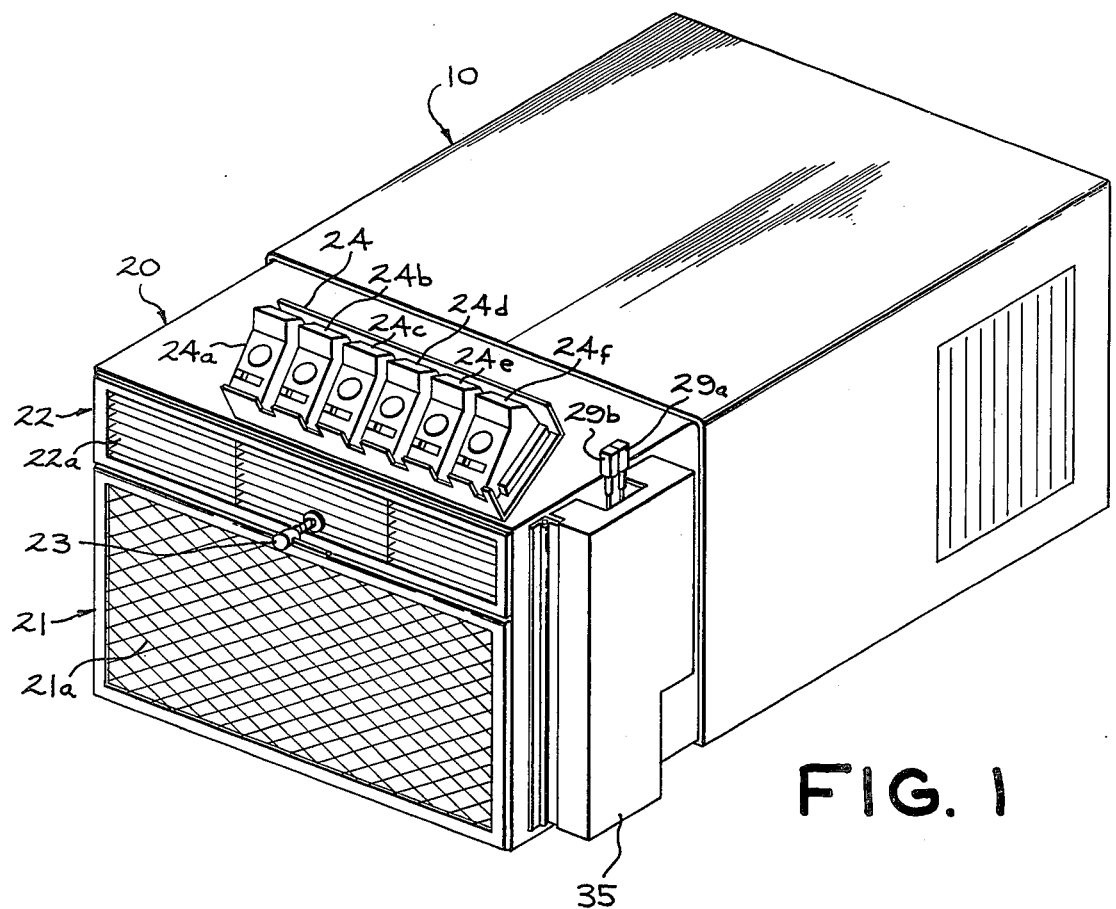
FIG. 1 is a perspective view of an air conditioner to the front of which portable psychrometric test apparatus is attached for operation of the present invention.

Referring to FIG. 1, there is shown portable psychrometric test apparatus 20 constructed in accordance with the present invention and mounted on the front of a conventional air conditioner 10 in course of performing the method of the present invention. The test apparatus 20 is held on the front of air conditioner 10 in air sealed manner by a latch 23. Test apparatus 20 includes a first intake air flow chamber 21 which has a grille 21a fixed in place during the test procedure, the grille being preferably identical to that mounted on the air conditioner during its customary air cooling operation so as to provide an equivalent air pressure drop thereacross. Preferably the regular intake grille is removed during the test procedure. Test apparatus 20 also includes a second discharge air flow chamber 22 through which the cooled discharge air flows after passing over the conventional evaporator section located in the air side of the air conditioner. Discharge air chamber 22 also has a grille fixed in place which is preferably indentical to that of the standard air conditoner discharge grille so as to provide an air pressure drop thereacross which is equivalent to that exhibited by the standard grille. It should be noted that the standard grille is preferably not present during the test procedure so that the air flow of the air conditioner is not disturbed by the presence of the test chambers. It is possible, however, to perform the method of the present invention with the standard grille in place in which case a slight deterioration of the accuracy of the test result may occur. A removable cover 35 encloses wet bulb and dry bulb thermometers which may be of the solid state thermistor type and which are connected to meters 24a–24d on meter panel 24 by means of connecting wires (not shown).

Referring now to FIGS. 2 through 5, a conventional cooling air conditioner is shown comprising within its case 10a the usual evaporator section having an evaporator heat exchanger 11 and evaporator air blower 12 mounted on the air side of interior partition 10b. The fan motor 13, condenser fan 14, compressor 15 and condenser 16 are located on the outside section of the air conditioner 10. In all respects, air conditioner 10 is of conventional construction and does not form a part of this invention.

In accordance with one aspect of the present invention, there is provided portable psychrometric test apparatus 20 having air flow means, including air intake chamber 21 and air discharge chamber 22, for passing intake and discharge evaporator air therethrough in response to normal operation of the air conditioner. That is to say, no auxiliary air blowers or plenums are used to force air across the measurement zones within each air chamber 21 and 22, the test apparatus itself being a passive device except for the air sampling devices described below. The air chambers are mutually isolated from each other and, when attached to the air conditioner, are mounted thereto in air sealed manner, there being a seal or gasket 36 extending around the periphery of the air conditioner case and also along the edge of the partition 10c separating the intake and discharge portion of the evaporator section. Preferably the cross-sectional areas of the air flow chambers 21 and 22 are generally coextensive with the cooperating openings of the air conditioner, however, it will be understood that there may be some overlap with the control panel 18 of the air conditioner.

Means, including latch 23, are provided for detachably securing test apparatus 20 to the front of the air conditioner. Latch handle 23a extends through the front of the test grille and is connected by rod 23d to a latch hook 23b which engages a strike or keeper column 23c. A compression spring 23e retains the hook in place during the test procedure and allows for ready removal of the test apparatus 20 at the completion of the test. Keeper 23c may be the conventional keeper mounted within the air conditioner for retention of the standard air discharge grill. The bottom of test apparatus is held in place by retainer hooks 23f which engage the lower lip 23g of the air conditioner case 10a.

Samples of the intake air are withdrawn from air flow chamber 21 by means of an air suction blower 32 the intake of which is coupled via air conduit 30a–30b to an elongate perforated air sampling tube 26 extending across air flow chamber 21 transverse to the direction of air flow through the chamber 21. Perforations 26a are directed outwardly into the face of the incoming air. Similarly, discharge air samples are withdrawn from air flow chamber 22 by means of air suction blower 33 whch is coupled via air conduit 31a–30b to perforated air sampling tube 27 extending across air flow chamber 22 transverse to the direction of air flow through chamber 22 with the tube perforations 27a being directed inwardly into the face of the discharge air.

A set of wet bulb and dry bulb thermometers 28a–28b and 29a–29b are positioned respectively within each air conduit 30a–30b and 31a–31b to provide measurement of wet bulb and dry bulb temperatures of each of the air samples at the end of a predetermined period of normal operation of the air conditioner 10. In accordance with one novel aspect of this invention, it has been determined that operation of an air conditioner for a limited period of time, such as fifteen minutes, will cause it to reach an interim stage of operating stability which will provide performance data in terms of changes in air enthalpy that will be entirely satisfactory to provide reasonably acccurate data for determining the operating capacity of the air conditioner as though it had been allowed to operate for enough time, such as one or two hours, to have delivered and stabilized water to the condenser coils. While fifteen minutes is considered to be the minimum suitable time for this purpose some deviation from this time is permissible within the spirit of the invention.

As is well known, in order to determine operating capacity using the change of air enthalpy method, it is necessary to know the mass flow rate of the conditioned air. Ths is determined by the inclusion in the test apparatus 20 of means, such as a small vane type anemometer 34, positioned within the intake air flow chamber 21 to measure the velocity of air flowing therethrough. This miniaturized device is preferably positioned behind conventional air flow straightening vanes (not shown) mounted in the intake grille of the test apparatus 20. The output of anemometer 34 is coupled to a meter 24c. Additionally, means including a thermometer 38 electrically coupled to meter 24f and temrorarily clipped onto the back of the air conditioner 10 are provided for measuring the dry bulb temperature of the environmental air outside of the test apparatus preferably in the vicinity of the air conditioner condenser air inlet. Thermometers 28a, 28b, 29a, 29b and 38 may each be a solid state thermistor type such as are marketed as fever thermometers by Electromedics, Inc. of Denver, Colorado.

Power outlet 37 is mounted on the side of test apparatus 20 to provide convenient source of power for operating air conditioner 10 during the test procedure. The upper receptacle 37b of outlet 37 may be coupled to a source of 220 volt power while the lower receptacle 37a may be coupled to a source of 110 volt power thus making test apparatus 20 suitably adapted to perform tests on a variety of air conditioner sizes. For convenience in determining the energy efficiency fo the air conditioner under test, the outlet 37 may be connected to the power supplies through conventional watt meters (not shown).

Figure 6:
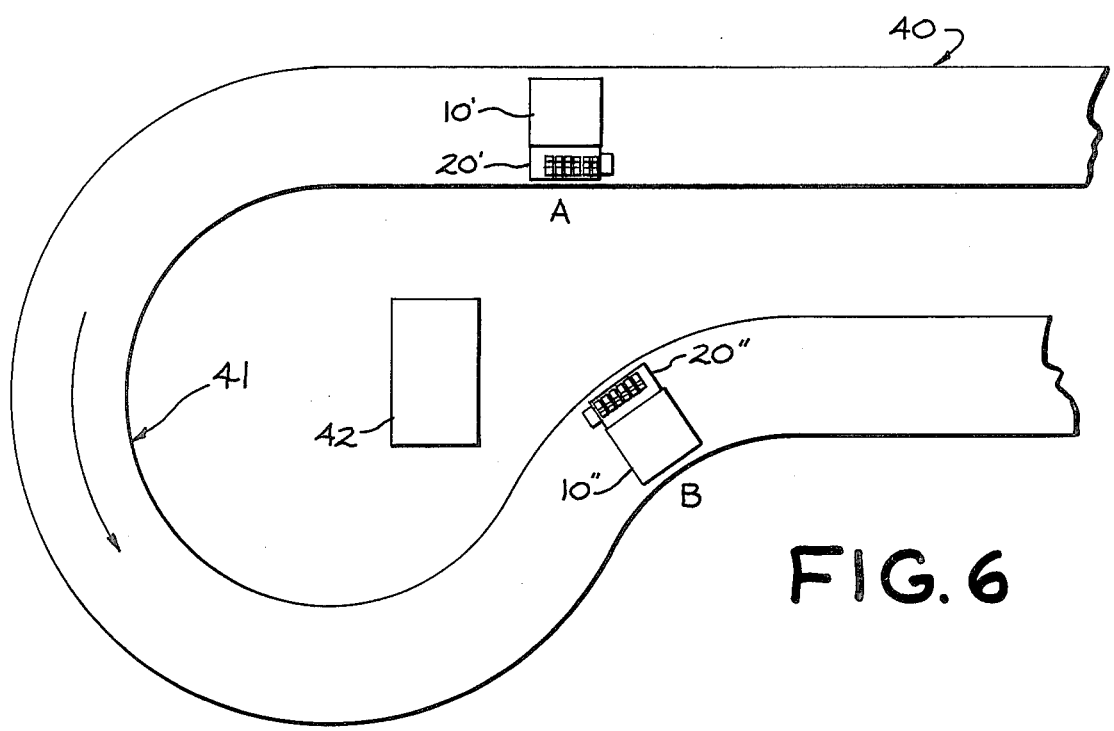
FIG. 6 is a schematic representation of a portion of a production line illustrating the performance of the method of the present invention.
Figure 3:
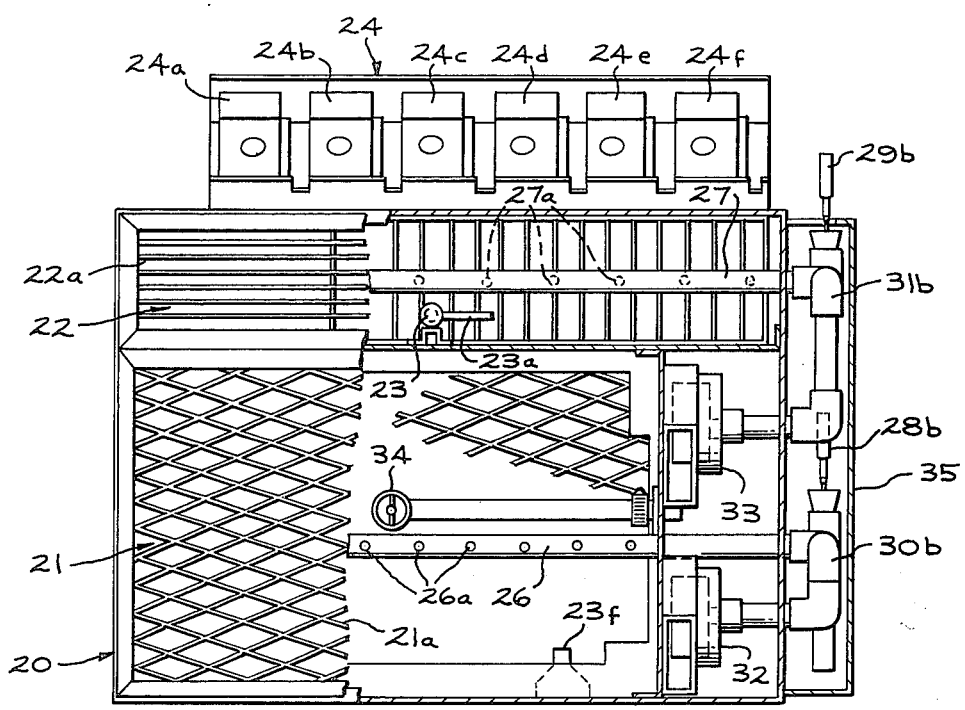
FIGS. 2 and 3 are side and front elevational views of the test apparatus of FIG. 1 shown partly broken away and partly in section to illustrate various structural features of the apparatus of the present invention.
Figure 2:
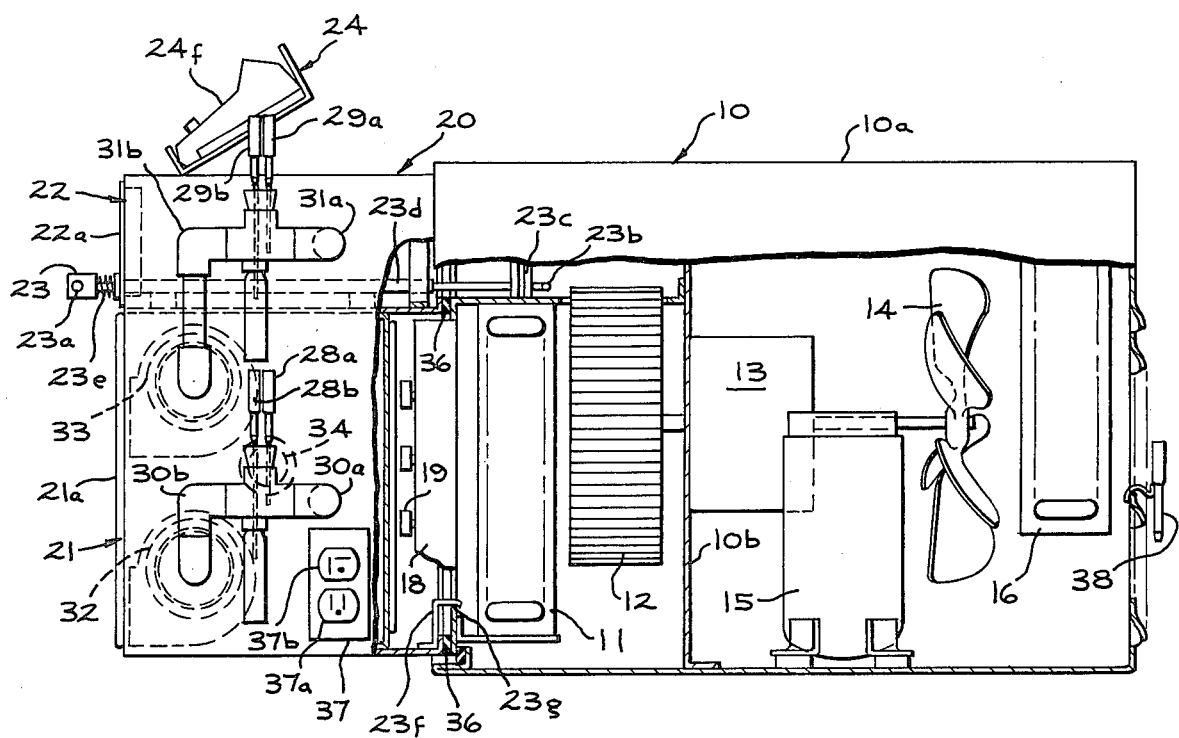
Figure 4:
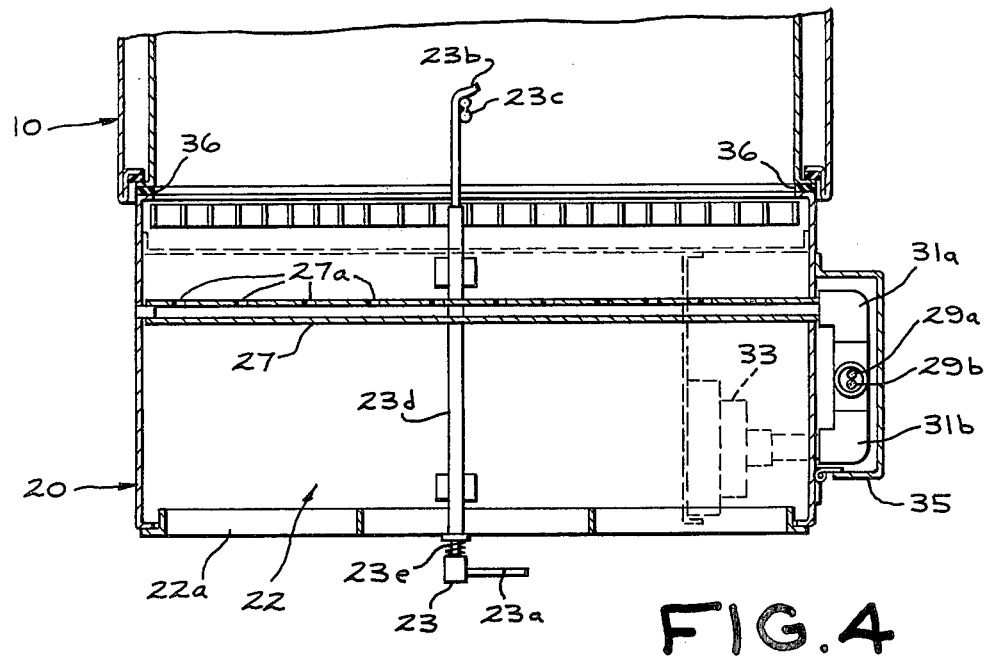
FIGS. 4 and 5 are cross-section plan views of the air discharge and air intake air flow chambers respectively of the test apparatus of FIG. 1.
Figure 5:
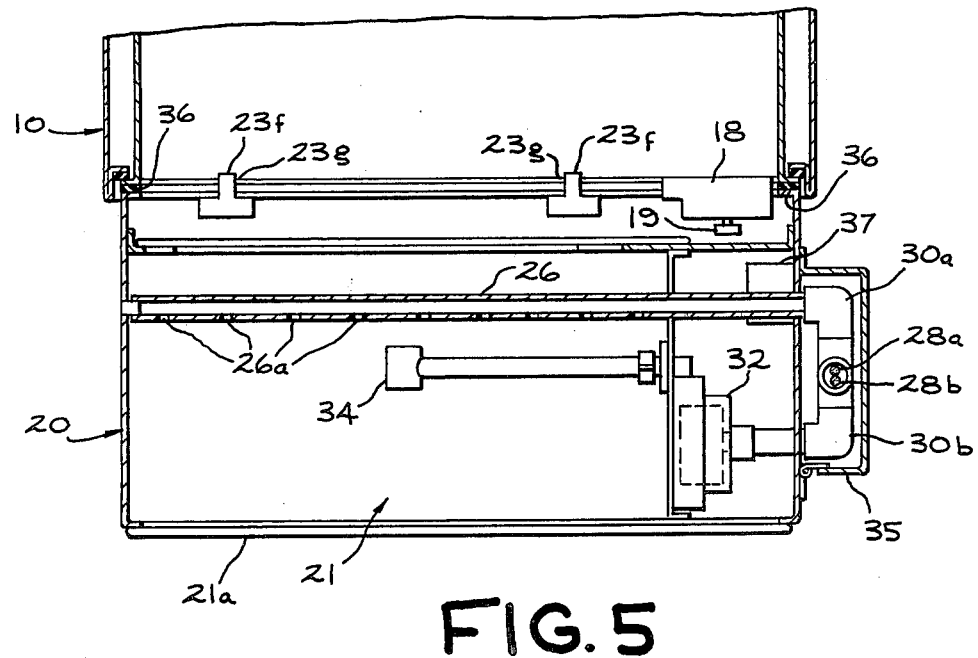

The method of the present invention may be performed on air conditioners at any location but is ideally suited for 100% audit testing at the end of a production line to assure, within statistically measurable accuracy, that the air conditioners are in compliance with governmental regulations on rating labels. In this aspect of the method as illustrated in FIG. 6, there is shown schematically a production line 40 having a loop section 41 of conveyor belt commencing at station A and ending at station B. The speed of the conveyor is set so that the time for an air conditioner to travel between stations A and B is approximately fifteen mintues or slightly longer. As air conditioner 10' enters the test loop at station A, a test operator turns the air conditioner control knob 19 to the "on" position, attaches the portable pyschrometric test apparatus 20' by means of latch 23, after removing the air conditioner front grille assuming it had been previously attached. The operator then places dry bulb thermometer 38 adjacent the air conditioner condenser inlet, and plugs the air conditioner into the power outlet on test apparatus 20'. Having completed this task, the operator then turns to face air conditioner 10" which has completed its travel around the loop section 41, thus having been in normal operation for the aforementioned approximately fifteen minute duration, and reads the temperature and air velocity measurements appearing on the meters 24a-24f.

With these measurements, it is a simple matter to determine the in situ operating capacity, Q, from the well known thermodynamic relationship:

$$Q_T = M(H_I - H_O)$$

where
Q_T is the total heat being substracted during the in situ test in BTU's per hour,
M is the mass flow rate of dry air flowing through the air chambers in pounds per hour,
$H_I$ and $H_O$ are the input and output air enthalpys of the conditioned air expressed in BTU's per pound of dry air.

At the same time, the operator reads the input test watts from which the test EER is determined:

$$EER_T = Q_T/W_T$$

In practice, the readings taken by the operator may be entered into a minicomputer 42 positioned adjacent to stain B of the test line 40. The minicomputer 42 may be conventionally programmed to calculate the in situ operating capacity and EER of air conditioner 10" in accordance with the foregoing expressions. Computer 42 is further programmed utilizing conventional programming techniques to operate so as to convert the in situ operating capacity and EER to the operating capacity and EER that this air conditioner 10" would exhibit under standard environmental test conditions by multiplying the in situ results by correction factors K and K' defined by the following expressions:

$$K = K_o + K_1 H_i + K_2 T_o$$

and $$K' = K'_o + K'_1 H_i + K'_2 T_o$$

where
$T_o$ is the temperature measured by the condenser dry bulb thermometer 38;
$H_i$ is the air inlet enthalpy;
$K_o$, $K'_o$, $K_1$, $K'_1$, $K_2$, $K'_2$ are constants determined emperically such as by "least squares" analysis of results taken from a series of tests under AHAM standard environmental test conditions performed on a plurality of air conditioners of the same design as unit 10".

Upon completion of the test, the operator removes the test apparatus at station B, turns and attaches it to the next air conditioner entering station A.

Mention is made above of deriving EER through these test measurements. It will be appreciated that it may be sufficient to simply determine in situ input power and convert that to power usage under standard conditions by means of a correction factor derived in the same manner as that explained above.

While the apparatus and method have been described in connection with a visual reading of test measurements on meters 24a-24f and manual insertion into computer 42, it will be appreciated that the electrical measurements can be coupled via appropriate signal cabling directly into the minicomputer 42 in digital form for direct computation. In this way, a simple go-no go indication can be utilized and the operator need only attach and detach the test apparatus, tagging the tested air conditioner with the appropriate indication as to whether or not it meets the desired test conditions corresponding to the rating label in question.

It has been found through experimentation that in situ testing of capacity in accordance with the present invention can produce extrapolated results which predict the operating capacity under standard conditions with sufficient statistical accuracy to assure reasonable compliance with rating label requirements in common factory ambient temperatures of from about 65° F. to about 100° F. and when measurements were taken after only fifteen minutes of operation.

The structure and operation of test apparatus 20 has been described in connection with a conventional room air conditioner. As will be readily apparent to those skilled in the art, the same test can be performed on packaged terminal air conditioners by sutiable modification of the air flow chamber configurations to conform with the intake and discharge grille openings of the unit under test. Additionally the test apparatus may be adapted for use on spit systems by employing separated air flow chambers, to permit their attachment to the openings of the air flow through configuration normally found in such systems. Finally, the apparatus and method of the present invention may also be used to determine, in like manner, capacity and efficiency under standard conditions of the heating section of an air conditioning unit.

The foregoing is a description of the preferred embodiment of the apparatus and method of the invention and variations may be made thereto without departing from the true spirit of the invention as defined by the appended claims.

What is claimed is:

1. Portable in situ psychrometric test apparatus for determining operating capacity of an air conditioner comprising:
   (a) air flow means for passing intake and discharge evaporator air therethrough in response to normal operation of the air conditioner, said air flow means having first and second mutually isolated air flow chambers adapted to be detachably secured in air sealed manner to the evaporator side of the air conditioner;
   (b) means for detachably securing the air flow means to the evaporator air side of the air conditioner;
   (c) means for withdrawing samples of the intake and discharge air from each of the first and second air flow chambers;
   (d) means for measuring the wet bulb and dry bulb temperatures of each of the air samples at the end of a predetermined period of normal operation;
   (e) means for measuring the velocity of a sample of the air flowing through at least one of said air flow chambers, said sample being less than the total volume of air flowing therethrough, and
   (f) means for measuring the dry bulb air temperature adjacent the environmental air inlet to the condenser side of the air conditioner.

2. Portable in situ psychrometric test apparatus for determining, without the use of standard environmental test rooms, the capacity that an air conditioner would exhibit when operated under predetermined standard environmental test conditions, said apparatus comprising:
   (a) air flow means for passing intake and discharge evaporator air therethrough in response to normal operation of the air conditioner, said air flow means having first and second mutually isolated air flow chambers adapted to be detachably secured in air sealed manner to the evaporator side of the air conditoner;
   (b) means for detachably securing the air flow means to the evaporator air side of the air conditoner;
   (c) means for withdrawing samples of the intake and discharge air from each of the first and second air flow chambers;
   (d) means for measuring the wet bulb and dry bulb temperatures of each of the air samples at the end of a predetermined period of normal operation;
   (e) means for measuring the velocity of the air flowing through the first air flow chamber at the end of said predetermined period of normal operation;
   (f) means for measuring dry bulb air temperature of the environmental air in the vicinity of the condenser air inlet outside the air flow chambers at the end of said predetermined period of normal operation;
   (g) whereby the in situ operating capacity of the air conditioner may be determined from said measurements and converted to operating capacity under standard environmental test conditions by application of a predetermined correction factor a function of said environmental air temperature derived empirically from multiple tests of a similar design air conditioner taken under the standard environmental test conditons.

3. The test apparatus of claim 1 in which the first and second air flow chambers are at least coextensive in cross-section with the evaporator air inlet and evaporator air outlet, respectively of the air conditioner.

4. The test apparatus of claim 1 or 2 in which the air sampling means for each chamber includes (a) an elongate perforated tube extending transverse to a substantial portion of the air flowing therethrough, (b) an air suction device and (c) air conduits connecting the air sampling tuber to the temperature measuring means and further connecting the temperature measuring means to the air suction device.

5. The test apparatus of claim 4 in which the air velocity measuring means comprises a vane type anemometer and the first air flow chamber has, at its inlet end, air straightening vanes to create a uniform velocity profile across the inlet area of the air flow chamber.

6. The test apparatus of claim 4 in which the temperature measuring means comprise solid state thermistor probes positioned within the path of the sampled air flowing through the conduit.

7. A method for determining, without the use of standard environmental test rooms, the operating capacity of an air conditioner under predetermine standard environmental test conditions comprising the steps of:
   (a) attaching air flow chambers in air sealed manner to the evaporator air side of the air conditioner in place of and in lieu of the normal air conditioner grille;
   (b) energizing the air conditioner for normal operation thereby causing air to flow through said chambers and across said evaporator;
   (c) withdrawing from each chamber samples of the air flowing therethrough;
   (d) measuring wet bulb and dry bulb temperatures of said air samples at least at the end of a predetermined period of normal operation of the air conditioner, said period being substantially less than required to cause condenser moisture to accumulate and throw water up to the condenser coils for stabilized operation;
   (e) measuring the velocity fo air flowing through the air chamber attached to the air inlet portion of the air conditioner;
   (f) measuring the dry bulb temperature of environmental air on the condenser side of the air conditioner at the end of said predetermined time period;
   (g) determining the in situ operating capacity of the air conditioner; and
   (h) converting the in situ capacity to operating capacity under standard environmanetal test conditions by application to the in situ result a predetermined correction factor derived empirically from multiple tests of similar air conditioners under said standard environmental test conditions.

8. The method of claim 7 further including the steps of determining in situ input power and converting the in situ input power to operating input power under standard environmental test conditions by application to the in situ result of a predetermined correction factor derived emperically from multiple tests of similar air conditioners under said standard environmental test conditions.

9. The method of claim 7 or 8 in which said predetermined period of normal operation is approximately fifteen minutes.

* * * * *